US00PP33368P2

(12) United States Plant Patent
Hatae

(10) Patent No.: US PP33,368 P2
(45) Date of Patent: Aug. 17, 2021

(54) ***CATHARANTHUS* PLANT NAMED 'SUNFS 82311'**

(50) Latin Name: *Catharanthus roseus*
Varietal Denomination: Sunfs 82311

(71) Applicant: Norihiko Hatae, Shiga (JP)

(72) Inventor: Norihiko Hatae, Shiga (JP)

(73) Assignee: SUNTORY FLOWERS LIMITED, Tokyo (JP)

( * ) Notice: Subject to any disclaimer, the term of this patent is extended or adjusted under 35 U.S.C. 154(b) by 0 days.

(21) Appl. No.: 16/926,743

(22) Filed: Jul. 12, 2020

(51) Int. Cl.
*A01H 5/02* (2018.01)
*A01H 6/08* (2018.01)

(52) U.S. Cl.
USPC ..... Plt./263.1
CPC ..... *A01H 6/084* (2018.05); *A01H 5/02* (2013.01)

(58) Field of Classification Search
USPC ..... Plt./263.1
See application file for complete search history.

*Primary Examiner* — Susan McCormick Ewoldt
(74) *Attorney, Agent, or Firm* — C. Anne Whealy

(57) ABSTRACT

A new and distinct cultivar of *Catharanthus* plant named 'Sunfs 82311', characterized by its compact, semi-upright and uniformly mounding plant habit; vigorous growth habit; freely basal branching habit; freely flowering habit; long flowering period; relatively small star-shaped purple-colored flowers with darker purple-colored centers; and good garden performance.

1 Drawing Sheet

Botanical designation: *Catharanthus roseus.*
Cultivar denomination: 'SUNFS 82311'.

BACKGROUND OF THE INVENTION

The present invention relates to a new and distinct *Catharanthus* plant, botanically known as *Catharanthus roseus* and hereinafter referred to by the cultivar name 'Sunfs 82311'.

The new *Catharanthus* plant is a product of a planned breeding program conducted by the Inventor in Gifu, Japan. The objective of the breeding program is to develop new compact and freely branching *Catharanthus* plants with numerous attractive flowers.

The new *Catharanthus* is a naturally-occurring whole plant mutation of a proprietary selection of *Catharanthus roseus* identified as code designation FS24-39, not patented. The new *Catharanthus* plant was discovered and selected by the Inventor as a single flowering plant from within a population of plants of the mutation parent in Gifu, Japan in June, 2016.

Asexual reproduction of the new *Catharanthus* plant by vegetative tip cuttings in a controlled greenhouse environment in Gifu, Japan since December, 2016, has shown that the unique features of this new *Catharanthus* plant are stable and reproduced true to type in successive generations.

SUMMARY OF THE INVENTION

Plants of the new *Catharanthus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunfs 82311'. These characteristics in combination distinguish 'Sunfs 82311' as a new and distinct *Catharanthus* plant:

1. Compact, semi-upright and uniformly mounding plant habit.
2. Vigorous growth habit.
3. Freely basal branching habit.
4. Freely flowering habit.
5 Long flowering period.
6. Relatively small star-shaped purple-colored flowers with darker purple-colored centers.
7. Good garden performance.

Plants of the new *Catharanthus* can be compared to plants of the mutation parent selection. Plants of the new *Catharanthus* differ primarily from plants of the mutation parent selection in flower color as plants of the *Catharanthus* have purple-colored flowers with darker purple-colored centers whereas plants of the mutation parent selection have red purple-colored flowers.

Plants of the new *Catharanthus* can be compared to plants of the *Catharanthus roseus* 'Suncatha 2439', disclosed in U.S. Plant Pat. No. 27,477. In side-by-side comparisons, plants of the new *Catharanthus* differ primarily from plants of 'Suncatha 2439' in the following characteristics:

1. Plants of the new *Catharanthus* are more compact than plants of 'Suncatha 2439'.
2. Plants of the new *Catharanthus* and 'Suncatha 2439' differ in flower color as plants of the new *Catharanthus* have purple-colored flowers with darker purple-colored centers whereas plants of 'Suncatha 2439' have flowers that are dark red purple in color.

BRIEF DESCRIPTION OF THE PHOTOGRAPHS

The accompanying colored photographs illustrate the overall appearance of the new *Catharanthus* plant showing the colors as true as it is reasonably possible to obtain in colored reproductions of this type. Colors in the photographs may differ slightly from the color values cited in the detailed botanical description which accurately describe the colors of the new *Catharanthus* plant.

The photograph at the top of the sheet is a side perspective view of a typical flowering plant of 'Sunfs 82311' grown in a container.

The photograph at the bottom of the sheet is a close-up view of a typical flowering plant of 'Sunfs 82311'.

DETAILED BOTANICAL DESCRIPTION

The aforementioned photographs and following observations, measurements and values describe plants grown during the summer in 15-cm containers in an outdoor nursery in Higashiomi, Shiga, Japan and under cultural practices typical of commercial production. During the production of the plants, day temperatures averaged 25° C. and night temperatures averaged 15° C. Plants were four months old when the photographs were taken and five months old when the description was taken. In the following description, color references are made to The Royal Horticultural Society Colour Chart, 2015 Edition, except where general terms of ordinary dictionary significance are used.

Botanical classification: *Catharanthus roseus* 'Sunfs 82311'.

Parentage: Naturally-occurring whole plant mutation of a proprietary selection of *Catharanthus roseus* identified as code designation FS24-39, not patented.

Propagation:

*Type*.—By vegetative tip cuttings.

*Time to initiate roots, summer*.—About two weeks at temperatures about 30° C.

*Time to initiate roots, winter*.—About three weeks at temperatures about 25° C.

*Time to produce a rooted young plant, summer*.—About five weeks at temperatures about 30° C.

*Time to produce a rooted young plant, winter*.—About six weeks at temperatures about 25° C.

*Root description*.—Fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Compact, semi-upright and uniformly mounding plant habit; freely basal branching habit with numerous basal and secondary branches developing per plant; vigorous growth habit.

*Plant height*.—About 24 cm.

*Plant diameter*.—About 38 cm.

Lateral branch description:

*Quantity per plant*.—About three primary lateral branches each with about six secondary lateral branches developing per plant; pinching is not required.

*Length*.—About 18 cm.

*Diameter*.—About 4.4 mm.

*Internode length*.—About 5.6 mm.

*Strength*.—Strong.

*Aspect*.—Upright to outwardly.

*Texture*.—Sparsely pubescent; rough.

*Color*.—Close to 64A.

Leaf description:

*Quantity and arrangement*.—About 24 per lateral branch; opposite, simple.

*Length*.—About 3.1 cm.

*Width*.—About 1.3 cm.

*Shape*.—Elliptical.

*Apex*.—Acute.

*Base*.—Obtuse.

*Margin*.—Entire.

*Texture, upper and lower surfaces*.—Sparsely pubescent.

*Venation pattern*.—Pinnate; reticulate.

*Color*.—Developing leaves, upper surface: Close to 138A. Developing leaves, lower surface: Close to 143A. Fully expanded leaves, upper surface: Close to 137A; venation, close to 144D. Fully expanded leaves, lower surface: Close to 143A; venation, close to 144D.

*Petioles*.—Length: About 3.7 mm. Diameter: About 1.2 mm. Texture, upper and lower surfaces: Sparsely pubescent. Color, upper and lower surfaces: Close to 144D tinged with close to 71B.

Flower description:

*Flower arrangement and habit*.—Single star-shaped salverform flowers arising from upper leaf axils; freely flowering habit with about 340 small flowers developing per plant; flowers face mostly upright.

*Fragrance*.—None detected.

*Flowering habit*.—Plants begin flowering about two to three weeks after planting; long flowering period, in the garden, plants flower continuously from the early summer to late autumn in Japan.

*Flower longevity*.—Individual flowers last about two to three days on the plant; flowers not persistent.

*Flower buds*.—Length: About 2.8 cm. Diameter: About 9.6 mm Shape: Ovoid with cylindrical tube. Color: Towards the base, close to 145D and towards the apex, close to 72B.

*Flower diameter*.—About 2.5 cm.

*Flower length* (*depth*).—About 2.4 cm.

*Tube length*.—About 2 cm.

*Tube diameter, proximally*.—About 1 mm.

*Tube diameter, distally*.—About 1.9 mm.

*Corolla*.—Arrangement: Five petals in a single whorl fused at the base into a tube. Petal length from throat: About 1.25 cm. Petal width: About 6.2 mm. Petal shape: Narrowly elliptic to oblanceolate. Petal apex: Cuspidate. Petal margin: Entire; none to slight undulation. Petal texture, upper and lower surfaces: Smooth, glabrous. Throat texture: Smooth, glabrous. Tube texture: Smooth, glabrous. Color: Petal, when opening, upper surface: Close to 77A. Petal, when opening, lower surface: Close to N155D tinged with N75C. Petal, fully opened, upper surface: Close to N77B; towards the base, close to 77A; color becoming closer to N74D with development. Petal, fully opened, lower surface: Close to N155D tinged with close to N75C; color does not change with development. Throat: Proximally, close to 145C; distally, close to NN144C. Tube: Proximally, close to 145C; distally, close to 145A; tinged with close to 61A.

*Calyx*.—Arrangement: Star-shaped tubular calyx with five sepals fused towards the base. Length: About 1.4 mm. Diameter: About 1.5 mm. Sepal length: About 1.4 mm. Sepal width: About 0.9 mm. Sepal shape:

Lanceolate. Sepal apex: Acuminate. Sepal margin: Entire. Sepal texture, upper and lower surfaces: Sparsely pubescent. Color, upper and lower surfaces: Close to 143A.

*Peduncles*.—Length: About 1.5 mm. Diameter: About 1.2 mm. Angle: Upright to outwardly. Strength: Strong. Texture: Sparsely pubescent. Color: Close to 145B tinged with close to 61A.

*Reproductive organs*.—Stamens: Quantity per flower: Five. Anther size: About 1.4 mm by 0.5 mm. Anther shape: Narrowly elliptic. Anther color: Close to 149D. Pollen amount: Scarce. Pollen color: Close to 11D. Pistils: Quantity per flower: One. Pistil length: About 1.8 cm. Style color: Close to 144D. Stigma shape: Transversely ellipsoidal. Stigma color: Close to 143A. Ovary color: Close to 144D. Seeds and fruits: To date, seed and fruit development have not been observed on plants of the new *Catharanthus*.

Garden performance: Plants of the new *Catharanthus* have been observed to have good garden performance and to tolerate wind, rain and temperatures ranging from about 5° C. to about 35° C. to 40° C.

Pathogen & pest resistance: To date, plants of the new *Catharanthus* have not been observed to be resistant to pathogens and pests common to *Catharanthus* plants.

It is claimed:

1. A new and distinct *Catharanthus* plant named 'Sunfs 82311' as illustrated and described.

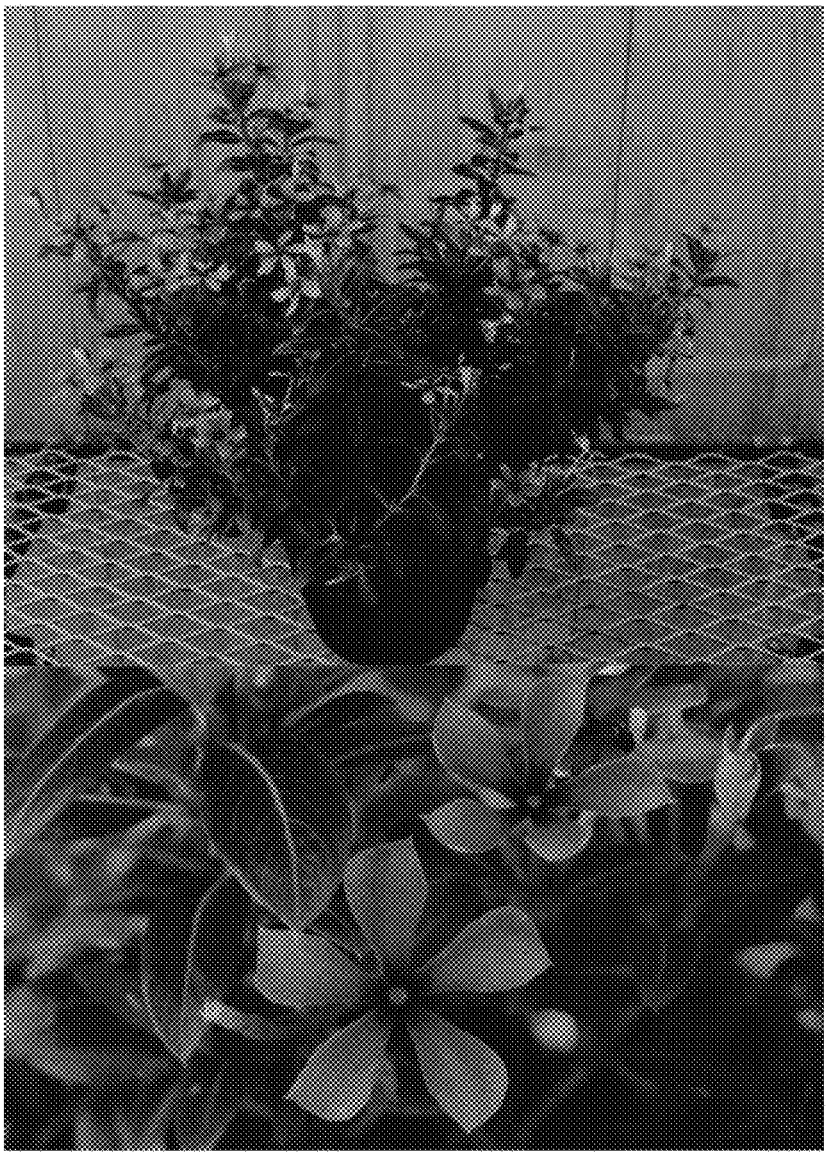

* * * * *